US009873846B2

(12) United States Patent
Hill et al.

(10) Patent No.: US 9,873,846 B2
(45) Date of Patent: *Jan. 23, 2018

(54) FUEL COMPOSITIONS CONTAINING LIGNOCELLULOSIC BIOMASS FERMENTATION PROCESS SYRUP

(71) Applicant: E I DU PONT DE NEMOURS AND COMPANY, Wilmington, DE (US)

(72) Inventors: Kenneth Miles Hill, Wilmington, DE (US); Steven H Swearingen, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/510,142

(22) Filed: Oct. 9, 2014

(65) Prior Publication Data
US 2015/0101242 A1 Apr. 16, 2015

Related U.S. Application Data

(60) Provisional application No. 61/889,061, filed on Oct. 10, 2013.

(51) Int. Cl.
| | |
|---|---|
| *C10L 5/14* | (2006.01) |
| *C10L 5/10* | (2006.01) |
| *C10L 5/44* | (2006.01) |
| *C10L 5/02* | (2006.01) |
| *C10L 9/10* | (2006.01) |
| *C05F 5/00* | (2006.01) |
| *C08K 13/02* | (2006.01) |
| *C12P 7/10* | (2006.01) |
| *C05D 9/00* | (2006.01) |
| *C10L 5/04* | (2006.01) |
| *C10L 5/36* | (2006.01) |

(52) U.S. Cl.
CPC .............. *C10L 5/445* (2013.01); *C05D 9/00* (2013.01); *C05F 5/008* (2013.01); *C08K 13/02* (2013.01); *C10L 5/02* (2013.01); *C10L 5/04* (2013.01); *C10L 5/14* (2013.01); *C10L 5/363* (2013.01); *C10L 5/442* (2013.01); *C10L 9/10* (2013.01); *C12P 7/10* (2013.01); *C10L 2200/0469* (2013.01); *C10L 2230/14* (2013.01); *C10L 2290/02* (2013.01); *C10L 2290/06* (2013.01); *C10L 2290/08* (2013.01); *C10L 2290/10* (2013.01); *C10L 2290/24* (2013.01); *C10L 2290/26* (2013.01); *C10L 2290/28* (2013.01); *C10L 2290/30* (2013.01); *C10L 2290/543* (2013.01); *C10L 2290/547* (2013.01); *Y02E 50/10* (2013.01); *Y02E 50/16* (2013.01); *Y02E 50/30* (2013.01)

(58) Field of Classification Search
CPC .... C10L 5/10; C10L 5/14; C10L 5/143; C10L 5/445; C10L 5/363; C10L 5/04; C10L 5/442; C10L 9/10; C10L 5/02; C10L 2290/06; C10L 2290/543; C10L 2290/02; C10L 2290/24; C10L 2290/28; C10L 2290/30; C10L 2290/547; C10L 2290/08; C10L 2290/10; C10L 2230/14; C10L 2200/0469; C10L 2290/26; C10L 2290/01012; C05F 5/008; C05D 9/00; C12P 7/10; C08K 13/02; Y02E 50/30; Y02E 50/16; Y02E 50/10
USPC .......................................... 44/550, 560, 605
See application file for complete search history.

(56) References Cited

U.S. PATENT DOCUMENTS

| | | | |
|---|---|---|---|
| 1,677,994 A | 7/1928 | Stillman | |
| 1,851,689 A | 3/1932 | Wolf | |
| 3,966,427 A | 6/1976 | Herment et al. | |
| 5,009,671 A | 4/1991 | Franke et al. | |
| 5,242,470 A * | 9/1993 | Salter .................. | C10L 5/14 44/552 |
| 5,580,389 A | 12/1996 | Farone et al. | |
| 5,743,924 A * | 4/1998 | Dospoy .................... | C10L 5/04 44/553 |
| 5,916,826 A | 6/1999 | White | |
| 6,686,194 B1 | 2/2004 | Mutzel et al. | |
| 7,629,156 B2 | 12/2009 | Viitanen et al. | |
| 7,741,119 B2 | 6/2010 | Viitanen et al. | |
| 7,781,191 B2 | 8/2010 | Dunson, Jr. et al. | |
| 7,915,017 B2 | 3/2011 | Dale | |
| 7,932,063 B2 | 4/2011 | Dunson, Jr. et al. | |
| 7,998,713 B2 | 8/2011 | Dunson, Jr. et al. | |
| 8,247,208 B2 | 8/2012 | Caimi et al. | |
| 8,476,048 B2 | 7/2013 | Caimi et al. | |

(Continued)

FOREIGN PATENT DOCUMENTS

| | | |
|---|---|---|
| AU | 2010364515 A1 | 7/2013 |
| CN | 1327960 A | 12/2001 |

(Continued)

OTHER PUBLICATIONS

International Search Report and Written Opinion, PCT Application PCT/US2014/060034, dated Apr. 2, 2015 (Corresponds to US Publication 2015-0104842-A1).
International Search Report and Written Opinion, PCT Application PCT/US2014/060038; dated Jan. 14, 2015. (Corresponds to US Publication 2015-0101242-A1).
Lynd et al., Microbial Cellulose Utilization: Fundamentals and Biotechnology, Microbiology and Molecular Biology Reviews, vol. 66, No. 3 (2002), pp. 506-577.

(Continued)

*Primary Examiner* — Pamela H Weiss

(57) ABSTRACT

A solid lignocellulosic fuel composition is produced from combining the syrup co-product of a lignocellulosic biomass fermentation process and an additional fuel component. The syrup is an excellent binder for a powdery fuel material that is not readily handled. The fuel composition is further processed to form briquettes, pellets and the like.

20 Claims, No Drawings

(56) References Cited

U.S. PATENT DOCUMENTS

| | | |
|---|---|---|
| 8,545,633 B2 | 10/2013 | Nguyen |
| 8,721,794 B2 | 5/2014 | Hennessey |
| 2001/0042494 A1 | 11/2001 | Welshimer et al. |
| 2004/0049973 A1* | 3/2004 | Donovan ............ C10L 5/02 44/500 |
| 2007/0031918 A1* | 2/2007 | Dunson, Jr. ............ C12P 7/08 435/41 |
| 2008/0274235 A1* | 11/2008 | Kor ............ C10L 1/023 426/54 |
| 2010/0166913 A1 | 7/2010 | Stewart |
| 2010/0183783 A1 | 7/2010 | Meier |
| 2010/0331580 A1 | 12/2010 | Ridgley |
| 2012/0102823 A1 | 5/2012 | Hennessey |
| 2012/0102828 A1 | 5/2012 | Hennessey et al. |
| 2012/0178976 A1 | 7/2012 | Hennessey et al. |
| 2015/0101242 A1 | 4/2015 | Hill |
| 2015/0101377 A1 | 4/2015 | Deruyter |
| 2015/0101378 A1 | 4/2015 | Ogle |
| 2015/0101511 A1 | 4/2015 | Deruyter |
| 2015/0101751 A1 | 4/2015 | Ogle |
| 2015/0104842 A1 | 4/2015 | Hill |

FOREIGN PATENT DOCUMENTS

| | | | |
|---|---|---|---|
| DE | 411324 C | 3/1925 | |
| DE | 475429 C | 4/1929 | |
| DE | 3821950 A1 | 1/1990 | |
| GB | 13914 | 0/1906 | |
| GB | 190506784 A * | 0/1906 | |
| GB | 190513914 A * | 0/1906 | ............ C10L 5/445 |
| GB | 190519212 A * | 0/1906 | |
| WO | 2010113129 A2 | 10/2010 | |
| WO | 2010113130 A2 | 10/2010 | |
| WO | 2011002660 A1 | 1/2011 | |
| WO | 2011038019 A2 | 3/2011 | |
| WO | WO 2011133571 A2 * | 10/2011 | ............ C08H 8/00 |
| WO | 2011137147 A1 | 11/2011 | |
| WO | WO 2011137147 A1 * | 11/2011 | ............ C10L 1/00 |
| WO | 2012069665 A1 | 5/2012 | |
| WO | 2012077124 A2 | 6/2012 | |
| WO | 2012103220 A1 | 8/2012 | |
| WO | 2013029171 A1 | 3/2013 | |
| WO | 2014026048 A2 | 2/2014 | |

OTHER PUBLICATIONS

Penttila et al., A Versatile Transformation System for the Cellulolytic Filamentous Fungus Trichoderma Reesei, Gene, Vol. 61 (1987), pp. 155-164.

Sheir-Neiss et al., Characterization of the Secreted Cellulases of Trichoderma Reesei Wild Type and Mutants During Controlled Fermentations, Appl. Microbiol. Biotechnol., vol. 20 (1984), pp. 46-53.

International Search Report and Written Opinion, PCT Application PCT/US2014/060040, dated Jan. 14, 2015. (Corresponds to US Publication 2015-0101377-A1).

International Search Report and Written Opinion, PCT Application PCT/US2014/060043, dated Jan. 14, 2015, (Corresponds to US Publication 2015-0101378-A1).

International Search Report and Written Opinion, PCT Application PCT/US2014/060045, dated Jan. 13, 2015. (Corresponds to US Publication 2015-0101511-A1).

International Search Report and Written Opinion, PCT Application PCT/US2014/060046, dated Jan. 13, 2015. (Corresponds to US Publication 2015-0101751-A1).

Kim et al., Composition of Corn Dry-Grind Ethanol By-Products: DDGS, Wet Cake and Thin Stillage, Bioresource Technology, vol. 99 (2008); pp. 5165-5176.

Noureddini et al., Dilute-Acid Pretreatment of Distillers Grains and Corn Fiber, Bioresource Technology, vol. 101 (2010), pp. 1060-1067.

* cited by examiner

FUEL COMPOSITIONS CONTAINING LIGNOCELLULOSIC BIOMASS FERMENTATION PROCESS SYRUP

This application claims the benefit of U.S. Provisional Application 61/889061, filed Oct. 10, 2013, now pending, which is incorporated in its entirety herein by referenced.

FIELD OF THE INVENTION

The invention relates to the field of composite fuel compositions. More specifically, the syrup co-product of a lignocellulosic biomass fermentation process is an excellent binder in fuel compositions.

BACKGROUND OF THE INVENTION

There are number of materials that have value as fuels, but are in a form that is intractable for use as a fuel in terms of handling. For example, coal mining, processing, and handling produces millions of tons of coal fines that cannot be readily burned as fuel due to issues with handling and transport. Coal fines may be made into usable fuel by combining and compacting with other materials such as a starch/oil emulsion (U.S. Pat. No. 1,851,689), starch and molasses (U.S. Pat. No. 5,009,671), asphaltic binder material (U.S. Pat. No. 823,025), bitumen binders (U.S. Pat. No. 3,966,427), or liquefied biomass (U.S. Pat. No. 5,916,826). Extrusion and pelletizing processes have been used to make readily transportable and easily handled fuel pellets containing coal fines.

There are additional materials that have fuel value, but are powdery or granular and thus not amenable to fuel use. These materials could be used as fuel if they could be made into a convenient, easily handled product. This includes biomass materials such as wood dust, milled biomass, and co-products from processes that use lignocellulosic biomass.

In a cellulosic ethanol process which makes use of lignocellulosic biomass as a carbon source for fermentation, whole stillage from a distillation column (beer column) is typically separated into solids (wetcake or filter cake) and liquid (thin stillage) fractions. The thin stillage is passed through evaporators producing a syrup. The filter cake and syrup are co-products of the cellulosic ethanol process. A syrup with at least about 40% solids may be burned as disclosed in U.S.20120102823, thereby providing energy. The filter cake may also be burned to provide energy.

There remains a need for compositions of materials that are convenient to handle and useful as burnable fuels, that are made from materials that are otherwise difficult to use as fuels.

SUMMARY OF THE INVENTION

The invention provides a solid fuel that is a mixture of syrup produced from a process that starts with lignocellulosic biomass and an additional fuel material. The additional fuel material is typically one that is not readily handled for use as a fuel.

Accordingly, the invention provides a lignocellulosic syrup composition comprising:
a) from about 40% to about 70% solids;
b) from about 10 g/l to about 30 g/l of acetamide;
c) at least about 40 g/l of sugars;
wherein the lignocellulosic syrup has a density of about 1 to about 2 g/cm$^3$ and a viscosity of less than 500 SSU at 100° F. (38° C.).

In another aspect, the invention provides a solid lignocellulosic fuel composition comprising:
a) lignocellulosic syrup composition comprising:
  i) from about 40% to about 70% solids;
  ii) from about 10 g/l to about 30 g/l of acetamide;
  iii) at least about 40 g/l of sugars;
    wherein the lignocellulosic syrup has a density of about 1 to about 2 g/cm$^3$ and a viscosity of less than 500 SSU at 100° F. (38° C.); and
b) at least one additional fuel component.

In yet another aspect, the invention provides a wet lignocellulosic filter cake composition comprising:
a) from about 35% to about 65% moisture;
b) from about 20% to about 75% volatiles;
c) from about 35% to about 65% solids;
d) from about 1% to about 30% ash content; and
e) from about 5% to about 20% fixed carbon;
wherein the filter cake composition has an energy value of about 2,000 to about 9,000 BTU/lb.

In yet another aspect the invention provides solid lignocellulosic fuel composition comprising lignocellulosic syrup composition above and lignocellulosic filter cake composition above.

In yet another aspect the invention provides a process for the production of a solid lignocellulosic fuel composition comprising mixing the lignocellulosic syrup composition above with at least one additional fuel component to produce a solid lignocellulosic fuel composition.

In yet another aspect the invention provides a process for the production of ethanol from a lignocellulosic biomass comprising:
a) providing a steam powered lignocellulosic ethanol production system comprising:
  i) a means for reducing the particle size of the biomass;
  ii) a means for pretreating biomass for the release of polymeric sugars;
  iii) a means for converting the polymeric sugars of ii) to monomeric sugars;
  iv) a means for the conversion of the monomeric sugars of iii) to ethanol; and
  v) a means for the recovery of the ethanol of iv);
wherein the lignocellulosic ethanol production system produces:
1) a lignocellulosic syrup composition comprising:
  a) from about 40% to about 70% solids;
  b) from about 10 g/l to about 30 g/l of acetamide;
  c) at least about 40 g/l of sugars; and
  d) at least about 5 g/l of ammonia;
    wherein the lignocellulosic syrup has a density of about 1 to about 2 g/cm$^3$ and a viscosity of less than 500 SSU at 100° F. (38° C.); and
2) a wet lignocellulosic filter cake composition comprising:
  a) from about 35% to about 65% moisture;
  b) from about 20% to about 75% volatiles;
  c) from about 35% to about 65% solids;
  d) from about 1% to about 30% ash content; and
  e) from about 5% to about 20% fixed carbon;
    wherein the filter cake composition has an energy value of about 2,000 to about 9,000 BTU/lb;
    wherein the lignocellulosic syrup composition and the wet lignocellulosic filter cake are used to generate steam to power the lignocellulosic ethanol production system.

DETAILED DESCRIPTION

Fuel materials that are difficult to use due to physical properties, such as small particle size making a dusty, powdery, or granular material, can be mixed with another material to form a usable fuel material such as pellets or briquettes. A syrup produced from a fermentation process that uses lignocellulosic biomass is an excellent binder for powdery fuel materials such as coal fines, filter cake that is also produced from a lignocellulosic biomass fermentation process, and other particulate biomass. The syrup has value itself as a fuel, and when mixed with a particulate second fuel component, binds the second fuel component such that the mixture can be extruded and/or formed to make a useful solid fuel product. The lignocellulosic fermentation process syrup co-product is low-cost, low in moisture, and a fuel in itself making it valuable in a solid lignocellulosic fuel composition.

The following definitions and abbreviations are to be used for the interpretation of the claims and the specification.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "fermentable sugar" refers to oligosaccharides and monosaccharides that can be used as a carbon source by a microorganism in a fermentation process.

The term "lignocellulosic" refers to a composition comprising both lignin and cellulose. Lignocellulosic material may also comprise hemicellulose.

The term "cellulosic" refers to a composition comprising cellulose and additional components, including hemicellulose.

The term "saccharification" refers to the production of fermentable sugars from polysaccharides.

The term "pretreated biomass" means biomass that has been subjected to pretreatment prior to saccharification. The pretreatment may take the form of physical, thermal or chemical means and combinations thereof.

The term "butanol" refers to isobutanol, 1-butanol, 2-butanol, or combinations thereof.

The term "lignocellulosic biomass" refers to any lignocellulosic material and includes materials comprising cellulose, hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Lignocellulosic biomass includes, but is not limited to, bioenergy crops, agricultural residues, municipal solid waste, industrial solid waste, sludge from paper manufacture, yard waste, wood and forestry waste. Examples of biomass include, but are not limited to, corn cobs, crop residues such as corn husks, corn stover, grasses (including Miscanthus), wheat straw, barley straw, hay, rice straw, switchgrass, waste paper, sugar cane bagasse, sorghum material, soybean plant material, components obtained from milling of grains or from using grains in production processes (such as DDGS: dried distillers grains with solubles), trees, branches, roots, leaves, wood chips, sawdust, shrubs and bushes, vegetables, fruits, flowers, empty palm fruit bunch, and energy cane.

The term "energy cane" refers to sugar cane that is bred for use in energy production. It is selected for a higher percentage of fiber than sugar.

The term "lignocellulosic biomass hydrolysate" refers to the product resulting from saccharification of lignocellulosic biomass. The biomass may also be pretreated or pre-processed prior to saccharification.

The term "lignocellulosic biomass hydrolysate fermentation broth" is broth containing product resulting from biocatalyst growth and production in a medium comprising lignocellulosic biomass hydrolysate. This broth includes components of lignocellulosic biomass hydrolysate that are not consumed by the biocatalyst, as well as the biocatalyst itself and product made by the biocatalyst.

The term "slurry" refers to a mixture of insoluble material and a liquid. A slurry may also contain a high level of dissolved solids. Examples of slurries include a saccharification broth, a fermentation broth, and a stillage.

The term "whole stillage" refers to the bottoms of a distillation. The whole stillage contains the high boilers and any solids of a distillation feed stream. Whole stillage is a type of depleted broth.

The term "thin stillage" refers to a liquid fraction resulting from solid/liquid separation of a whole stillage, fermentation broth, or product depleted fermentation broth.

The term "product depleted broth" or "depleted broth" refers herein to a lignocellulosic biomass hydrolysate fermentation broth after removal of a product stream.

The term "syrup" means a concentrated product produced from the removal of water, generally by evaporation, from thin stillage.

The term "target product" refers to any product that is produced by a microbial production host cell in a fermentation. Target products may be the result of genetically engineered enzymatic pathways in host cells or may be produced by endogenous pathways. Typical target products include but are not limited to acids, alcohols, alkanes, alkenes, aromatics, aldehydes, ketones, biopolymers, proteins, peptides, amino acids, vitamins, antibiotics, and pharmaceuticals.

The term "fermentation" refers broadly to the use of a biocatalyst to produce a target product. Typically the biocatalyst grows in a fermentation broth utilizing a carbon source in the broth, and through its metabolism produces a target product.

The term "solid lignocellulosic fuel composition" refers to a mixture of lignocellulosic syrup and an additional fuel component. It includes an initial mixture of these components, as well as the mixture at any stage following mixing. It thus includes the composition during and after processing to form a readily handled fuel material.

"Solids" refers to soluble solids and insoluble solids. Solids from a lignocellulosic fermentation process contain residue from the lignocellulosic biomass used to make hydrolysate medium.

"Volatiles" refers herein to components that will largely be vaporized in a process where heat is introduced. Volatile content is measured herein by establishing the loss in weight resulting from heating under rigidly controlled conditions to 950° C. (as in ASTM D-3175). Typical volatiles include, but are not limited to, hydrogen, oxygen, nitrogen, acetic acid, and some carbon and sulfur.

"Fixed carbon" refers herein to a calculated percentage made by summing the percent of moisture, percent of ash, and percent of volatile matter, and then subtracting that percent from 100.

"Ash" is the weight of the residue remaining after burning under controlled conditions according to ASTM D-3174.

"Sugars" as referred to in the lignocellulosic syrup composition means a total of monosaccharide and soluble oligosaccharides.

Production and Composition of Syrup

The present lignocellulosic syrup is produced as a co-product from a process that uses lignocellulosic biomass as a source of fermentable sugars which are used as a carbon source for a biocatalyst. The biocatalyst uses the sugars in a fermentation process to produce a target product.

To produce fermentable sugars from lignocellulosic biomass, the biomass is treated to release sugars such as glucose, xylose, and arabinose from the polysaccharides of the biomass. Lignocellulosic biomass may be treated by any method known by one skilled in the art to produce fermentable sugars in a hydrolysate. Typically the biomass is pretreated using physical, thermal and/or chemical treatments, and saccharified enzymatically. Thermo-chemical pretreatment methods include steam explosion or methods of swelling the biomass to release sugars (see for example WO2010113129; WO2010113130). Chemical saccharification may also be used. Physical treatments for pre-processing the biomass include, but are not limited to, grinding, milling, and cutting.

Physical treatments such as these may be used for particle size reduction prior to further chemical treatment. Chemical treatments include base treatment such as with strong base (ammonia or NaOH), or acid treatment (U.S. Pat. No. 8,545,633; WO2012103220). In one embodiment the biomass is treated with ammonia (U.S. Pat. Nos. 7,932,063; 7,781,191; 7,998,713; 7,915,017).

These treatments release polymeric sugars from the biomass. Particularly useful is a low ammonia pretreatment where biomass is contacted with an aqueous solution comprising ammonia to form a biomass-aqueous ammonia mixture where the ammonia concentration is sufficient to maintain alkaline pH of the biomass-aqueous ammonia mixture but is less than about 12 weight percent relative to dry weight of biomass, and where dry weight of biomass is at least about 15 weight percent solids relative to the weight of the biomass-aqueous ammonia mixture, as disclosed in U.S. Pat. No. 7,932,063, which is herein incorporated by reference.

Saccharification, which converts polymeric sugars to monomeric sugars, may be either by enzymatic or chemical treatments. The pretreated biomass is contacted with a saccharification enzyme consortium under suitable conditions to produce fermentable sugars. Prior to saccharification, the pretreated biomass may be brought to the desired moisture content and treated to alter the pH, composition or temperature such that the enzymes of the saccharification enzyme consortium will be active. The pH may be altered through the addition of acids in solid or liquid form. Alternatively, carbon dioxide ($CO_2$), which may be recovered from fermentation, may be utilized to lower the pH. For example, $CO_2$ may be collected from a fermenter and fed into the pretreatment product headspace in the flash tank or bubbled through the pretreated biomass if adequate liquid is present while monitoring the pH, until the desired pH is achieved. The temperature is brought to a temperature that is compatible with saccharification enzyme activity, as noted below. Typically suitable conditions may include temperature between about 40° C. and 50° C. and pH between about 4.8 and 5.8.

Enzymatic saccharification of cellulosic or lignocellulosic biomass typically makes use of an enzyme composition or blend to break down cellulose and/or hemicellulose and to produce a hydrolysate containing sugars such as, for example, glucose, xylose, and arabinose. Saccharification enzymes are reviewed in Lynd, L. R., et al. (Microbiol. Mol. Biol. Rev., 66:506-577, 2002). At least one enzyme is used, and typically a saccharification enzyme blend is used that includes one or more glycosidases. Glycosidases hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem., 223:1-5, 1994; Eur. J. Biochem., 232:1-6, 1995; Eur. J. Biochem., 237:1-5, 1996; Eur. J. Biochem., 250:1-6, 1997; and Eur. J. Biochem., 264:610-650 1999, respectively]) of the general group "hydrolases" (EC 3.). Glycosidases useful in saccharification can be categorized by the biomass components they hydrolyze. Glycosidases useful in saccharification may include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabino-xylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), or feruloyl esterases (EC 3.1.1.73) to promote the release of polysaccharides from other components of the biomass. It is known in the art that microorganisms that produce polysaccharide-hydrolyzing enzymes often exhibit an activity, such as a capacity to degrade cellulose, which is catalyzed by several enzymes or a group of enzymes having different substrate specificities. Thus, a "cellulase" from a microorganism may comprise a group of enzymes, one or more or all of which may contribute to the cellulose-degrading activity. Commercial or non-commercial enzyme preparations, such as cellulase, may comprise numerous enzymes depending on the purification scheme utilized to obtain the enzyme. Many glycosyl hydrolase enzymes and compositions thereof that are useful for saccharification are disclosed in WO 2011/038019. Additional enzymes for saccharification include, for example, glycosyl hydrolases that hydrolyze the glycosidic bond between two or more carbohydrates, or between a carbohydrate and a noncarbohydrate moiety.

Saccharification enzymes may be obtained commercially. Such enzymes include, for example, Spezyme® CP cellulase, Multifect® xylanase, Accelerase® 1500, Accellerase® DUET, and Accellerase® Trio™ (Dupont™/Genencor®, Wilmington, Del.), and Novozyme-188 (Novozymes, 2880 Bagsvaerd, Denmark). In addition, saccharification enzymes may be unpurified and provided as a cell extract or a whole cell preparation. The enzymes may be produced using recombinant microorganisms that have been engineered to express one or more saccharifying enzymes. For example, an H3A protein preparation that may be used for saccharification of pretreated cellulosic biomass is an unpurified preparation of enzymes produced by a genetically engineered strain of *Trichoderma reesei*, which includes a combination of cellulases and hemicellulases and is described in WO 2011/038019, which is incorporated herein by reference.

Chemical saccharification treatments may be used and are known to one skilled in the art, such as treatment with mineral acids including HCl and $H_2SO_4$ (U.S. Pat. No. 5,580,389; WO2011002660).

Sugars such as glucose, xylose and arabinose are released by saccharification of lignocellulosic biomass and these monomeric sugars provide a carbohydrate source for a biocatalyst used in a fermentation process. The sugars are present in a biomass hydrolysate that is used as fermentation medium. The fermentation medium may be composed solely of hydrolysate, or may include components additional to the hydrolysate such as sorbitol or mannitol at a final concentration of about 5 mM as described in U.S. Pat. No. 7,629,156, which is incorporated herein by reference. The biomass hydrolysate typically makes up at least about 50% of the fermentation medium. Typically about 10% of the final volume of fermentation broth is seed inoculum containing the biocatalyst.

The medium comprising hydrolysate is fermented in a fermenter, which is any vessel that holds the hydrolysate fermentation medium and at least one biocatalyst, and has valves, vents, and/or ports used in managing the fermentation process.

Any biocatalyst that produces a target product utilizing glucose and preferably also xylose, either naturally or through genetic engineering, may be used for fermentation of the fermentable sugars in the biomass hydrolysate made from lignocellulosic biomass. Target products that may be produced by fermentation include, for example, acids, alcohols, alkanes, alkenes, aromatics, aldehydes, ketones, biopolymers, proteins, peptides, amino acids, vitamins, antibiotics, and pharmaceuticals. Alcohols include, but are not limited to methanol, ethanol, propanol, isopropanol, butanol, ethylene glycol, propanediol, butanediol, glycerol, erythritol, xylitol, mannitol, and sorbitol. Acids may include acetic acid, formic acid, lactic acid, propionic acid, 3-hydroxypropionic acid, butyric acid, gluconic acid, itaconic acid, citric acid, succinic acid, 3-hydroxyproprionic acid, fumaric acid, maleic acid, and levulinic acid. Amino acids may include glutamic acid, aspartic acid, methionine, lysine, glycine, arginine, threonine, phenylalanine and tyrosine. Additional target products include methane, ethylene, acetone and industrial enzymes.

The fermentation of sugars in biomass hydrolysate to target products may be carried out by one or more appropriate biocatalysts, that are able to grow in medium containing biomass hydrolysate, in single or multistep fermentations. Biocatalysts may be microorganisms selected from bacteria, filamentous fungi and yeast. Biocatalysts may be wild type microorganisms or recombinant microorganisms, and may include, for example, organisms belonging to the genera of *Escherichia, Zymomonas, Saccharomyces, Candida, Pichia, Streptomyces, Bacillus, Lactobacillus*, and *Clostridiuma*. Typical examples of biocatalysts include recombinant *Escherichia coli, Zymomonas mobilis, Bacillus stearothermophilus, Saccharomyces cerevisiae, Clostridia thermocellum, Thermoanaerobacterium saccharolyticum*, and *Pichia stipitis*. To grow well and have high product production in a lignocellulosic biomass hydrolysate fermentation broth, a biocatalyst may be selected or engineered to have higher tolerance to inhibitors present in biomass hydrolysate such as acetate. For example, the biocatalyst may produce ethanol as a target product, such as production of ethanol by *Zymomonas mobilis* as described in U.S. Pat. No. 8,247,208, which is incorporated herein by reference.

Fermentation is carried out with conditions appropriate for the particular biocatalyst used. Adjustments may be made for conditions such as pH, temperature, oxygen content, and mixing. Conditions for fermentation of yeast and bacterial biocatalysts are well known in the art.

In addition, saccharification and fermentation may occur at the same time in the same vessel, called simultaneous saccharification and fermentation (SSF). In addition, partial saccharification may occur prior to a period of concurrent saccharification and fermentation in a process called HSF (hybrid saccharification and fermentation).

For large scale fermentations, typically a smaller culture of the biocatalyst is first grown, which is called a seed culture. The seed culture is added to the fermentation medium as an inoculum typically in the range from about 2% to about 20% of the final volume. Typically fermentation by the biocatalyst produces a fermentation broth containing the target product made by the biocatalyst. For example, in an ethanol process the fermentation broth may be a beer containing from about 6% to about 10% ethanol. In addition to target product, the fermentation broth contains water, solutes, and solids from the hydrolysate medium and from biocatalyst metabolism of sugars in the hydrolysate medium. Typically the target product is isolated from the fermentation broth producing a depleted broth, which may be called whole stillage. For example, when ethanol is the product, the broth is distilled, typically using a beer column, to generate an ethanol product stream and a whole stillage. Distillation may be using any conditions known to one skilled in the art including at atmospheric or reduced pressure. The distilled ethanol is further passed through a rectification column and molecular sieve to recover an ethanol product. The target product may alternatively be removed in a later step such as from a solid or liquid fraction after separation of fermentation broth.

The syrup co-product of a lignocellulosic biomass fermentation process is produced from the fermentation broth or depleted fermentation broth. An example of syrup production is disclosed in U.S.20120102823, which is incorporated herein by reference. The broth or depleted broth, such as whole stillage, is separated into solid and liquid streams, where the liquid stream is called thin stillage.

Various filtration devices may be used such as a belt filter, belt press, screw press, drum filter, disc filter, Nutsche filter, filter press or filtering centrifuge. Filtration may be aided such as by application of vacuum, pressure, or centrifugal force. To improve efficiency of filtration, a heat treatment may be used as disclosed in commonly owned and copending U.S.20120178976, which is incorporated herein by reference.

Following liquid/solid separation of a lignocellulosic biomass hydrolysate fermentation broth or depleted broth, the solids fraction, or filter cake (also called wetcake), may be burned to supply energy to the production process. The filter cake may be dried prior to burning, such as by air drying, to reduce moisture.

A product stream may be removed following liquid/solid filtration of a lignocellulosic biomass hydrolysate fermentation broth. For example, the liquid stream may be extracted or distilled to generate a product stream, such as distillation to produce an ethanol product stream and a remaining liquid.

The liquid fraction is further purified by evaporation producing water that may be recycled and a syrup. Prior to evaporation, a portion of the liquid fraction may be recycled for use as back set, which may be added at any point in the process where water is needed, such as in pretreatment, saccharification, or biocatalyst seed production. Evaporation may be in any evaporation system, such as falling film, rising film, forced circulation, plate or mechanical and thermal vapor recompression systems. Evaporation may be continuous or batch and may use a multi-effect evaporator. The evaporated water may be recycled in the overall lignocellulosic biomass hydrolysate fermentation process.

The remaining material after evaporation is a syrup which is the present lignocellulosic syrup. The lignocellulosic syrup composition contains from about 40% to about 70% solids (may have about 40%, 45%, 50%, 55%, 60%, 65%, or 70% solids), from about 10 g/l to 30 g/l of acetamide, at least about 40 g/l of sugars, a density of about 1 to about 2 g/cm$^3$, and viscosity less than 500 SSU at 100° F. (38° C.). "SSU" is Saybolt Universal Viscosity in Seconds. When biomass is treated with ammonia, the lignocellulosic syrup contains at least about 5 g/l of ammonia. When biomass is treated with ammonia, the lignocellulosic syrup contains at least about 5 g/l of ammonia.

Additional Fuel Component

An additional fuel component is combined with the present lignocellulosic syrup to produce the present solid lignocellulosic fuel composition. Any material that is mixable and can be burned may be used as an additional fuel component. Typically the additional fuel component is a material that is particulate, and is powdery, dusty, or granular. In one embodiment the additional fuel component is coal fines. Coal fines typically have a particle size that is less than 0.0625 inch (0.159 cm), and may contain occasional particles up to about 0.125 inch (0.318 cm) and rarely larger, forming a dusty, powdery material. A typical batch of coal fines may have a moisture content that is up to about 15%, with lower moisture levels in batches that have been allowed to dry, such as under storage conditions.

In another embodiment the additional fuel component is filter cake produced from a lignocellulosic biomass fermentation process as described above. The filter cake may be used wet, or it may be dried which is typically by air drying. The wet lignocellulosic filter cake composition contains from about 35% to 65% moisture, or from about 40% to about 60% moisture (may have about 35%, 40%, 45%, 50%, 55%, 60%, or 65% moisture), from about 20% to about 75% volatiles or about 20% to about 40% volatiles (may have about 20%, 25%, 30%, 35%, 40%, 45%, 50%, 55%, 60%, 65%, or 75% volatiles), from about 35% to 65% solids or from about 40% to about 60% solids (may have about 35%, 40%, 45%, 50%, 55%, 60%, or 65% solids), from about 1% to about 30% ash, or from about 3% to about 30% ash (may have about 1%, 3%, 5%, 10%, 15%, 20%, 25%, or 30% ash), from about 5% to about 20% fixed carbon, and it has an energy value of about 2,000 to about 9,000 BTU/lb (may have about 2,000, 2,500, 3,000, 3,500, 4,000, 4,500, 5,000, 5,500, 6,000, 6,500, 7,000, 7,500, 8,000, 8,500, or 9,000 BTU/lb). The volatile content is measured by establishing the loss in weight resulting from heating under rigidly controlled conditions to 950° C. (as in ASTM D-3175). Typical volatiles include hydrogen, oxygen, nitrogen, acetic acid, and some carbon and sulfur. Ash is determined by weighing the residue remaining after burning under controlled conditions according to ASTM D-3174. The amount of fixed carbon is calculated by adding the percentages of moisture, ash, and volatiles, and then subtracting from 100. The full upper range of BTU/lb is typically achieved with drying. Filter cake may be dried and/or processed into particles prior to using, such as in a hammermill. In another embodiment the additional fuel component is particulate petroleum coke (also called petcoke). Petcoke is a solid carbonaceous material that is a side product of oil refining or other cracking processes. It is a product of refining oil sands. Petcoke may be of any type such as green coke, needle coke, acicular coke, fuel grade coke, calcined petroleum coke, or desulphurized coke.

In various other embodiments the additional fuel component is biomass that has been size-reduced to produce a material that is mixable with lignocellulosic syrup. Any cellulosic biomass may be used as listed above. The biomass may be a waste product from a process such as in a wood, grain, or farming industry. This type of material may include materials such as sawdust, corn fiber, corn stover, corn cobb, and bagasse. The biomass may be newly harvested material such as switchgrass. The biomass may be size-reduced by any method known to one skilled in the art such as by grinding, milling, cutting, chopping, crushing, and/or disc refining. Typically the lignocellulosic biomass is reduced in size to particles that make a mixable material such as one that is granular, dusty, and/or powdery.

Solid Lignocellulosic Fuel Composition

The present solid lignocellulosic fuel composition contains the present lignocellulosic syrup and an additional fuel component, as described above. The present lignocellulosic syrup and additional fuel component are mixed together and formed into a lignocellulosic fuel composition. Typically the components are added together slowly or in increments while mixing to avoid clumping. Any type of mixer may be used such as a double paddle mixer or a mixer truck, depending on the scale needed.

The lignocellulosic syrup and additional fuel component are mixed in amounts such that the syrup is between about 10% and 50% of the final mixture of syrup and additional fuel component. The syrup may be about 10%, 15%, 20%, 25%, 30%, 35%, 40%, 45%, or 50% of the total mixture. In one embodiment the syrup is between about 20% and 40% of the final mixture of syrup and additional fuel component, and the additional fuel component is coal fines. In one embodiment the syrup is between about 10% and 40% of the final mixture of syrup and additional fuel component, and the additional fuel component is lignocellulosic filter cake.

The moisture content of the syrup may be about 40%. The moisture content of the additional fuel component may be 40% or higher such as for wetcake (filter cake) produced in a lignocellulosic biomass fermentation process or freshly harvested biomass. Each of these components may be dried prior to mixing to remove some moisture. For example, the additional fuel component may be dried, such as air drying, to reduce the moisture level to avoid clumping while mixing. The moisture content of the lignocellulosic fuel composition may be between about 10% and 40%, depending on drying of the materials. Drying may be of materials prior to mixing, after mixing, or after processing.

The mixture of lignocellulosic syrup and additional fuel component is processed to form a conveniently handled solid material. Processing may include treatments such as heating, compressing, extruding, pelleting, molding, and/or drying. Various shapes may be formed such as briquettes, pellets, irregular shapes, and the like. For example, the mixture may be passed through an extruder at an elevated temperature, then a pelletizer, then dried, forming hardened fuel pellets. Any type of extruder that pushes or draws semisoft solids through a die may be used, as known to one of skill in the art. Extrusion may be performed at elevated temperature and/or elevated pressure. A pelletizer may be used to reduce volume and increase density of the lignocellulosic fuel composition, either alone or combined with extrusion, and to form the material into pellets. Briquettes may be formed using a screw press or other compression apparatus. Following forming, the lignocellulosic fuel composition is allowed to dry forming a solid lignocellulosic fuel composition wherein the moisture content is less than 30%. The moisture may be less than about 30%, 25%, 20%, 15%, or 10% depending on the starting materials and the process used to produce the present solid lignocellulosic fuel composition.

Use of Solid Lignocellulosic Fuel Composition

The present solid lignocellulosic fuel composition is in a form that is readily handled and transported. The solid lignocellulosic fuel composition has much reduced dusting during handling, transport, and storage as compared to the additional fuel components alone. The solid lignocellulosic fuel composition may have reduced tendency to bridge and reduce flow out of a hopper. It may be burned in any appropriate burning furnace such as a steam boiler, hot water boiler, process furnace, or other industrial or commercial combustion process with suitable emissions controls.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "s" is second, "min" means minute(s), "h" of "hr" means hour(s), "µL" or "µl" means microliter(s), "mL" or "ml" means milliliter(s), "L" or "l" means liter(s), "m" is meter, "nm" means nanometer(s), "mm" means millimeter(s), "cm" means centimeter(s), "µm" means micrometer(s), "mM" means millimolar, "M" means molar, "mmol" means millimole(s), "µmole" means micromole(s), "g" means gram(s), "µg" means microgram(s), "mg" means milligram(s), "kg" is kilogram, "rpm" means revolutions per minute, "C" is Centigrade, "ppm" means parts per million, "cP" is centipoise, "g/l" means grams per liter, "SSU" is Saybolt Universal Viscosity in Seconds.

General Methods

Saccharification Enzymes

Accellerase® 1500 (A1500) and Multifect® Xylanase are obtained from Danisco U.S. Inc., Genencor, International (Rochester, N.Y.).

Cellulase and Hemicellulase Production Strain

Strain 229: A *Trichoderma reesei* strain, derived from RL-P37 (Sheir-Neiss and Montenecourt, 1984, Appl. Microbiol. Biotechnol. 20:46-53) through mutagenesis and selection for high cellulase production, was co-transformed with the β-glucosidase expression cassette (cbh1 promoter, *T. reesei* β-glucosidase1 gene, cbh1 terminator, and amdS marker), and the endoxylanase expression cassette (cbh1 promoter, *T. reesei* xyn3,and cbh1 terminator) using PEG mediated transformation (Penttila et al., 1987, Gene 61(2): 155-64). Numerous transformants were isolated and examined for β-glucosidase and endoxylanase production. One transformant, referred to as *T. reesei* strain #229, was used in certain studies described herein.

Strain H3A: *T. reesei* strain #229 was co-transformed with the (β-xylosidase Fv3A expression cassette (cbh1 promoter, Fv3A gene, cbh1 terminator, and alsR marker), the β-xylosidase Fv43D expression cassette (egl1 promoter, Fv43D gene, native Fv43D terminator), and the Fv51A α-arabinofuranosidase expression cassette (egl1 promoter, Fv51A gene, Fv51A native terminator) using electroporation. Transformants were selected on Vogels agar plates containing chlorimuron ethyl. Numerous transformants were isolated and examined for β-xylosidase and L-α-arabinofuranosidase production. *T. reesei* integrated expression strain H3A, which recombinantly expresses *T. reesei* β-glucosidase 1, *T. reesei* xyn3, Fv3A, Fv51A, and Fv43D was isolated."

Extra cellular protein produced during fermentation of strain H3A was separated from the cell mass by centrifugation, concentrated by membrane-ultrafiltration through a Millipore 10 kD molecular cut off weight membrane and pH adjusted to 4.8. Total protein was determined using a modified Biuret method as modified by Weichselbaum and Gornall using Bovine Serum Albumin as a calibrator (Weichselbaum, 1960, Amer. J. Clin. Path. 16:40; Gornall et al., 1949 J. Biol. Chem 177:752). This H3A extracellular protein preparation, called herein H3A protein, was used as a combination cellulase and hemicellulase preparation effecting complex carbohydrate hydrolysis during SSF.

Biocatalyst and Inoculum Preparation

Origin of the *Zymomonas mobilis* Strains for Fermentation

A lignocellulosic biomass hydrolysate fermentation broth may be made using alternative biocatalysts. Exemplary strains are are described below. As an alternative, strain ZW658, deposited as ATCC #PTA-7858, may be used to produce a lignocellulosic biomass hydrolysate fermentation broth for processing.

*Zymomonas mobilis* strain ZW705 was produced from strain ZW801-4 by the methods detailed in U.S. Pat. No. 8,247,208, which is herein incorporated by reference, as briefly restated here. Cultures of *Z. mobilis* strain ZW801-4 were grown under conditions of stress as follows. ZW801-4 is a recombinant xylose-utilizing strain of *Z. mobilis* that was described in U.S. Pat. No. 7,741,119, which is herein incorporated by reference. Strain ZW801-4 was derived from strain ZW800, which was derived from strain ZW658, all as described in U.S. Pat. No. 7,741,119. ZW658 was constructed by integrating two operons, PgapxylAB and Pgaptaltkt, containing four xylose-utilizing genes encoding xylose isomerase, xylulokinase, transaldolase and transketolase, into the genome of ZW1 (ATCC #31821) via sequential transposition events, and followed by adaptation on selective media containing xylose. ZW658 was deposited as ATCC #PTA-7858. In ZW658, the gene encoding glucose-fructose oxidoreductase was insertionally-inactivated using host-mediated, double-crossover, homologous recombination and spectinomycin resistance as a selectable marker to create ZW800. The spectinomycin resistance marker, which was bounded by loxP sites, was removed by site specific recombination using Cre recombinase to create ZW801-4.

A continuous culture of ZW801-4 was run in 250 ml stirred, pH and temperature controlled fermentors (Sixfors; Bottmingen, Switzerland). The basal medium for fermentation was 5 g/L yeast extract, 15 mM ammonium phosphate, 1 g/L magnesium sulfate, 10 mM sorbitol, 50 g/L xylose and 50 g/L glucose. Adaptation to growth in the presence of high concentrations of acetate and ammonia was effected by gradually increasing the concentration of ammonium acetate added to the above continuous culture media while maintaining an established growth rate as measured by the specific dilution rate over a period of 97 days. Ammonium acetate was increased to a concentration of 160 mM. Further increases in ammonium ion concentration were achieved by addition of ammonium phosphate to a final total ammonium ion concentration of 210 mM by the end of 139 days of continuous culture. Strain ZW705 was isolated from the adapted population by plating to single colonies and amplification of one chosen colony.

Strain AR3 7-31 was produced from strain ZW705 by further adaptation for growth in corn cob hydrolysate medium as disclosed in U.S. Pat. No. 8,476,048, which is incorporated herein by reference. ZW705 was grown in a turbidostat (U.S. Pat. No. 6,686,194; Heurisko USA, Inc. Newark, Del.), which is a continuous flow culture device where the concentration of cells in the culture was kept constant by controlling the flow of medium into the culture, such that the turbidity of the culture was kept within specified narrow limits. Two media were available to the growing culture in the continuous culture device, a resting medium (Medium A) and a challenge medium (Medium B). A culture was grown on resting medium in a growth chamber to a turbidity set point and then was diluted at a dilution rate set to maintain that cell density. Dilution was performed by adding media at a defined volume once every 10 minutes. When the turbidostat entered a media challenge mode, the choice of adding challenge medium or resting medium was made based on the rate of return to the set point after the previous media addition. The steady state concentration of medium in the growth chamber was a mix of Medium A and Medium B, with the proportions of the two media dependent upon the rate of draw from each medium that allowed maintenance of the set cell density at the set dilution rate. A sample of cells representative of the population in the growth chamber was recovered from the outflow of the turbidostat (in a trap chamber) at weekly intervals. The cell sample was grown once in MRM3G6 medium and saved as a glycerol stock at −80° C.

ZW705 was grown to an arbitrary turbidity set point that dictated that the culture use all of the glucose and approximately half of the xylose present in the incoming media to meet the set point cell density at the set dilution rate. Using resting medium that was 50% HYAc/YE and 50% MRM3G6.5x4.5NH4Ac12.3 and challenge medium that was HYAc/YE. A strain isolated after 3 weeks was used in another round of turbidostat adaptation using HYAc/YE as the resting medium and HYAc/YE+9 weight % ethanol as the challenge medium. Strain AR3 7-31 was isolated after 2 weeks and was characterized as a strain with improved xylose and glucose utilization, as well as improved ethanol production, in hydrolysate medium. By sequence analysis, AR3 7-31 was found to have a mutation in the *Zymomonas mobilis* genome ORF encoding a protein having characteristics of a membrane transport protein, and annotated as encoding a fusaric acid resistance protein.

Media

MRM3 contains per liter: yeast extract (10 g), $KH_2PO_4$ (2 g) and $MgSO_4.7H_2O$ (1 g)

MRM3G6 contains is MRM3 containing 60 g/L glucose

MRM3G6.5X4.5NH4Ac12.3 is MRM3 containing 65 g/L glucose, 45 g/L xylose, 12.3 g/L ammonium acetate HYAc/YE contains cob hydrolysate from which solids were removed by centrifugation and that was filter sterilized containing 68 g/L glucose, 46 g/L xylose and 5 g/L acetate, supplemented with 6.2 g/L ammonium acetate and 0.5% yeast extract, adjusted to pH5.8.

Lignocellulosic Biomass Processing and Fermentation

Corn stover is milled to ⅜" (0.95 cm). Pretreatment is at 140° C. with 14% $NH_3$ and 65% solids for 60 min. Saccharification is at 47° C., pH 5.3, with 7.8 mg / g glucan+xylan of an enzyme consortium, for 96 hr. Saccharification enzymes are a mix of cellulases and hemicellulases expressed in a *Trichoderma reesei* strain H3A as described above. The resulting hydrolysate is used in fermentation. 10 mM sorbitol is added to the hydrolysate making the fermentation medium, and the pH is adjusted to 5.8.

For the seed, first frozen strain *Zymomonas mobilis* AR3 7-31 stock is grown in MRM3G6 (10 g/L BBL yeast extract, 2 g/L KH2PO$_4$, 1 g/L MgSO$_4$*7H$_2$O, 60 g/L glucose) at 33° C., without shaking for 8 hr as a revival culture. MRM3G10 medium (same as MRM3G6 but with 100 g/L glucose) is inoculated with revival culture, and incubated at 33° C. with shaking for 14-16 hr. Growth is to an OD600 between 1.5 and 3.1. The entire culture is used to inoculate a seed fermenter to an initial OD600 of approximately 0.05.

The seed fermentation is carried out in 10 g/L yeast extract, 2 g/L KH2PO$_4$, 5 g/L MgSO$_4$*7H$_2$O, 10 mM sorbitol, and 150 g/L glucose. Seed fermentation is performed at 33° C. and pH 5.5. Seed is harvested after first observation of glucose reduction to less than 50 g/L, with glucose measured by using a YSI 2700 SELECT™ Biochemistry Analyzer (YSI Life Sciences; Yellow Springs, Ohio).

The seed is added to the hydrolysate medium in the fermenter. Fermentations are carried out at 30° C.-33° C. for 48-72 hr.

Lignocellulosic Syrup and Filter Cake

The fermentation broth is distilled to recover ethanol and the remaining whole stillage is filtered. The liquid fraction is passed through evaporators removing overhead water, and producing a lignocellulosic syrup. The solids fraction is a lignocellulosic filter cake.

Example 1

Prophetic Production of Fuel Pellets from Coal Fines and Lignocellulosic Syrup 50 pounds of coal fines with a moisture content of 8% are placed in an electric mixer. Syrup produced from a lignocellulosic biomass ethanol production process (see General Methods) is slowly poured into the coal fines while mixing. Batches are prepared with a final ratio of coal fines to syrup of 5:1 or 4:1. The resulting mixtures are each fed to an extruder that is run at a temperature of about 200° C. The extruded material is then fed to a pelletizer. The resulting pellets are allowed to cool and harden. The coal fines are held together in the resulting solid pellets, with little evidence of powdery material.

Example 2

Prophetic Production of Fuel Pellets from Filter Cake and Lignocellulosic Syrup 50 pounds of air-dried filter cake with a moisture content of 30% are hammer milled to particles and placed in an electric mixer. Syrup produced from a lignocellulosic biomass ethanol production process (see General Methods) is slowly poured into the filer cake while mixing. Batches are prepared with a final ratio of filter cake to syrup of 5:1 or 4:1. The resulting mixtures are each fed to an extruder that is run at a temperature of about 200° C. The extruded material is then fed to a pelletizer. The resulting pellets are allowed to cool and harden. The filterH cake particles are held together in the resulting solid pellets, with little evidence of powdery material.

What is claimed is:

1. A solid lignocellulosic fuel composition comprising a lignocellulosic syrup and at least one additional fuel component, wherein the lignocellulosic syrup comprises:
a) from 40% to 70% solids;
b) from 10 g/l to 30 g/l of acetamide;
c) at least 40 g/l of sugars;
wherein the lignocellulosic syrup has a density of 1 to 2 g/cm$^3$ and a viscosity of less than 500 SSU at 100° F. (38° C.).

2. The solid lignocellulosic fuel composition of claim 1 wherein the lignocellulosic syrup is the product of a process for the production of ethanol from a lignocellulosic biomass.

3. The solid lignocellulosic fuel composition of claim 2 wherein the lignocellulosic biomass is selected from the group consisting of corn cobs, corn stover, grasses, wheat straw, barley straw, hay, rice straw, switchgrass, waste paper, sugar cane bagasse, sorghum plant material, soybean plant material, woody plants, vegetables, fruits, flowers, empty palm fruit bunch, and energy cane.

4. The solid lignocellulosic fuel composition of claim 3 wherein the lignocellulosic biomass is corn stover.

5. The solid lignocellulosic fuel composition of claim 1 wherein the at least one additional fuel component is coal fines.

6. The solid lignocellulosic fuel composition of claim 1 wherein the at least one additional fuel component is a filter cake.

7. The solid lignocellulosic fuel composition of claim 6 wherein the filter cake is the product of a process for the production of ethanol from a lignocellulosic biomass.

8. The solid lignocellulosic fuel composition of claim 1 wherein the additional fuel component is at least one of petcoke and size-reduced biomass.

9. The solid lignocellulosic fuel composition of claim 1 wherein the solid lignocellulosic fuel composition comprises the lignocellulosic syrup in an amount of from 10% to 50% of the solid lignocellulosic fuel composition.

10. The solid lignocellulosic fuel composition of claim 9 wherein the solid lignocellulosic fuel composition comprises the lignocellulosic syrup in an amount of from 20% to 40% of the solid lignocellulosic fuel composition.

11. The solid lignocellulosic fuel composition of claim 1 having 10% to 40% moisture.

12. The solid lignocellulosic fuel composition of claim 1 wherein the lignocellulosic syrup is a co-product of a process for the production of alcohol from a lignocellulosic biomass which employs ammonia for the pretreatment of the lignocellulosic biomass, and the lignocellulosic syrup contains at least 5 g/l of ammonia.

13. A process for the production of a solid lignocellulosic fuel composition comprising mixing a lignocellulosic syrup with at least one additional fuel component to produce a solid lignocellulosic fuel composition, wherein the lignocellulosic syrup comprises:
a) from 40% to 70% solids;
b) from 10 g/l to 30 g/l of acetamide;
c) at least 40 g/l of sugars;
wherein the lignocellulosic syrup has a density of 1 to 2 g/cm$^3$ and a viscosity of less than 500 SSU at 100° F. (38° C.).

14. The process of claim 13 wherein the lignocellulosic syrup is the product of a process for the production of ethanol from a lignocellulosic biomass.

15. The process of claim 13 wherein the at least one additional fuel component is coal fines.

16. The process of claim 15 wherein the lignocellulosic syrup is mixed with the fuel component to a final ratio of coal fines to syrup of 5:1.

17. The process of claim 15 wherein the lignocellulosic syrup is mixed with the fuel component to a final ratio of coal fines to syrup of 4:1.

18. The process of claim 13 wherein the solid lignocellulosic fuel composition comprises the lignocellulosic syrup in an amount of from 10% to 50% of the solid lignocellulosic fuel composition.

19. The process of claim 13 wherein the at least one additional fuel component is a filter cake.

20. The process of claim 13 wherein the lignocellulosic syrup is a co-product of a process for the production of alcohol from a lignocellulosic biomass which employs ammonia for the pretreatment of the lignocellulosic biomass, and the lignocellulosic syrup contains at least 5 g/l of ammonia.

* * * * *